United States Patent
Bavendiek et al.

(10) Patent No.: US 6,687,328 B2
(45) Date of Patent: Feb. 3, 2004

(54) METHOD FOR INSPECTING OBJECTS PARTICULARLY FOR DETECTING DEFECTS OR IRREGULARITIES THEREIN BY MEANS OF X-RADIATION AND APPARATUS FOR PERFORMING THE METHOD

(75) Inventors: Klaus Bavendiek, Norderstedt (DE); Jürgen Bauer, Hamburg (DE)

(73) Assignee: Yxlon International X-ray GmbH, Hamburg (DE)

( * ) Notice: Subject to any disclaimer, the term of this patent is extended or adjusted under 35 U.S.C. 154(b) by 0 days.

(21) Appl. No.: 10/099,851

(22) Filed: Mar. 14, 2002

(65) Prior Publication Data

US 2003/0039332 A1 Feb. 27, 2003

(30) Foreign Application Priority Data

Mar. 24, 2001 (EP) ............................. 01107412

(51) Int. Cl.⁷ ................................. G21K 5/08
(52) U.S. Cl. ......................... 378/58; 378/208
(58) Field of Search ..................... 378/68, 69, 58, 378/208, 62

(56) References Cited

U.S. PATENT DOCUMENTS 4,422,177 A * 12/1983 Mastronardi et al. ......... 378/17
5,297,361 A    3/1994 Baldy et al. ................. 51/119
5,459,770 A   10/1995 Salje ........................... 378/71
5,848,115 A * 12/1998 Little et al. .................... 378/4
6,256,404 B1 * 7/2001 Gordon et al. ............. 382/131

FOREIGN PATENT DOCUMENTS

EP    09110359      10/1995
EP    0 959 344 A1  5/1998

* cited by examiner

Primary Examiner—Craig E. Church
Assistant Examiner—Hoon Song
(74) Attorney, Agent, or Firm—Roberts & Roberts, LLP

(57) ABSTRACT

The present invention relates to a method and an apparatus for the testing or inspection of objects, particularly for detecting defects or irregularities therein, by means of X-radiation, where the object to be inspected is brought into different spatial positions and stays there during image detection. For mechanical positioning of the objects, known methods and apparatuses require a relatively long time with limited inspection precision, while having a considerable space requirement. Accompanied by a small size, the invention obviates this problem in that the X-ray components, comprising X-ray tube and X-ray detector, are only moved in translatory manner and the inspection object or part in a gimbal suspension is only moved in rotary manner in at least one axis and a maximum of three axes x, y and z.

20 Claims, 11 Drawing Sheets

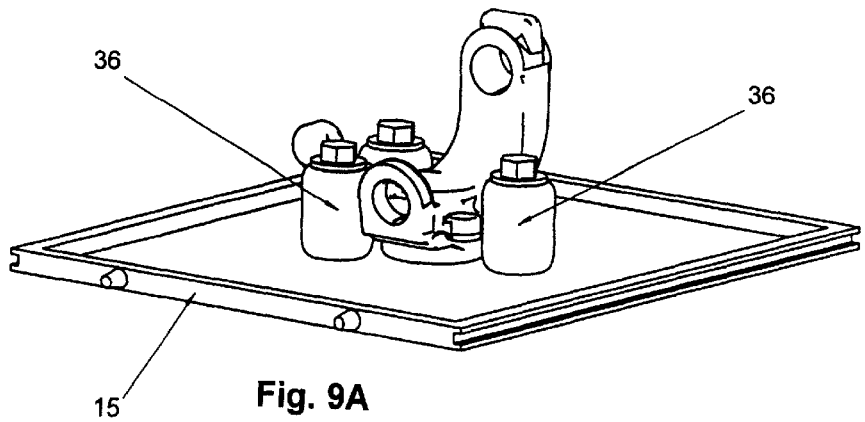
Fig. 9A
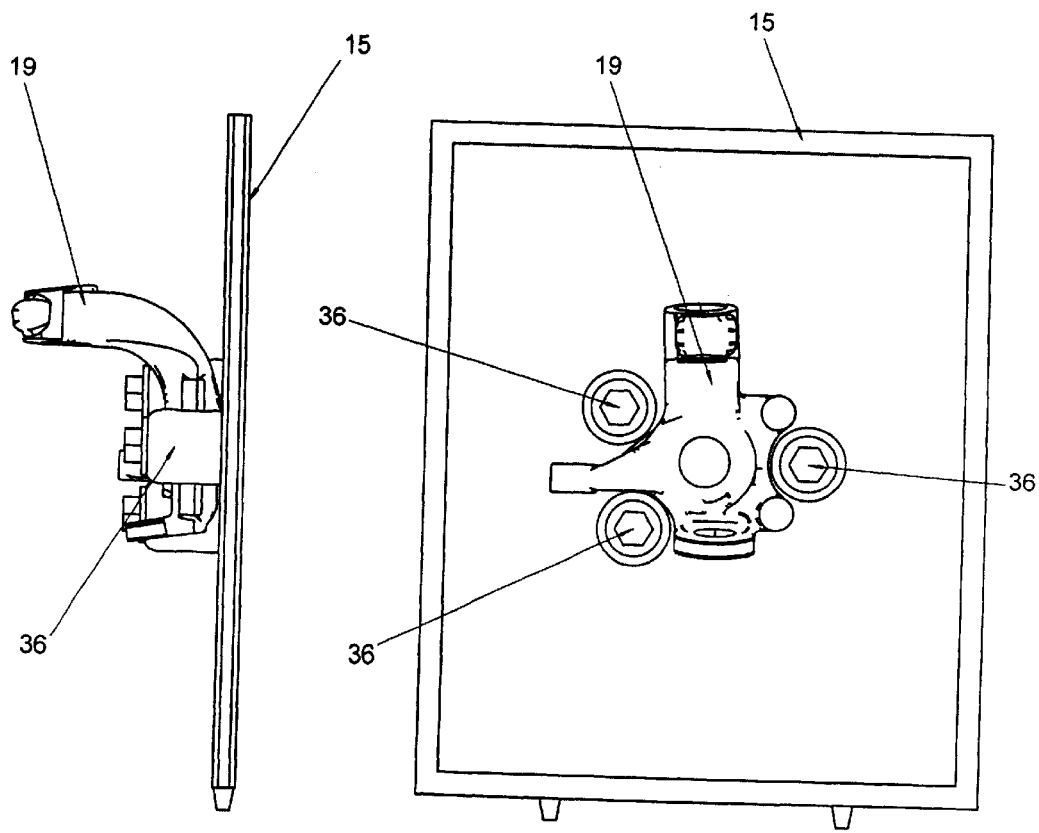
Fig. 9B
FIG. 9C

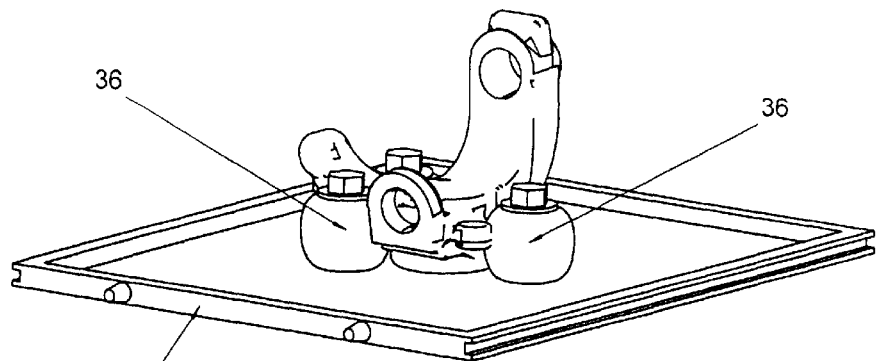
Fig. 10A
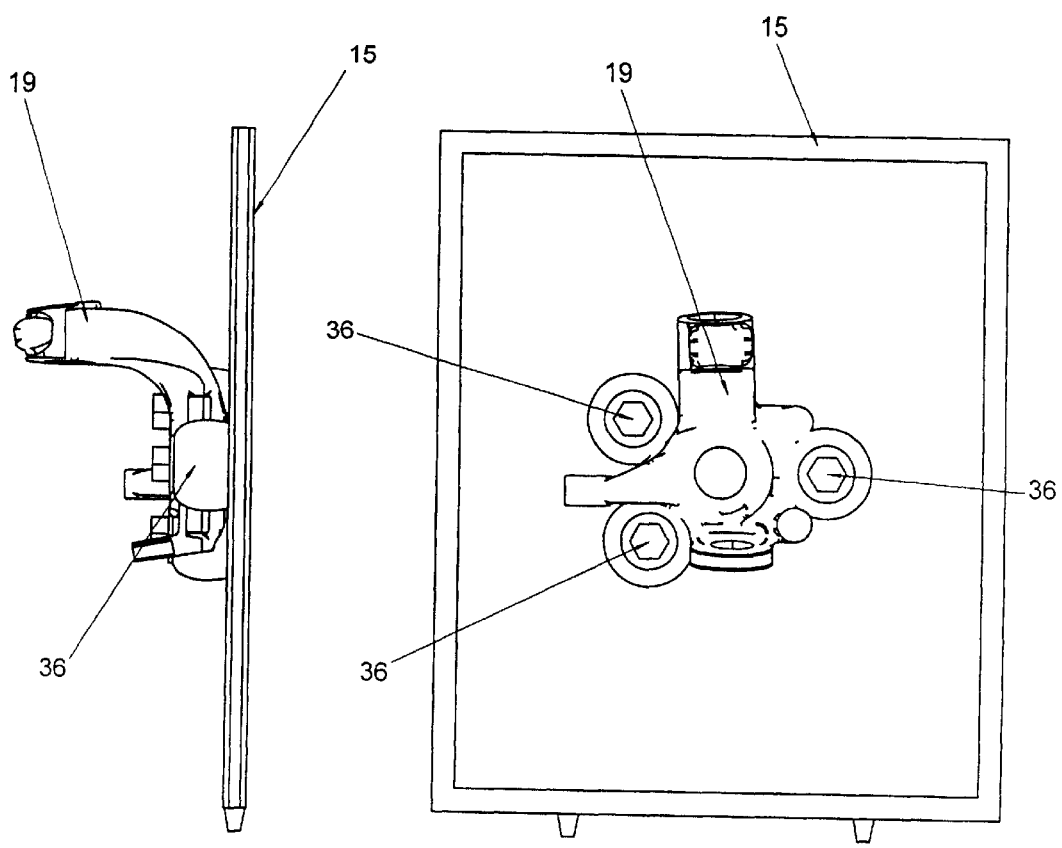
Fig. 10B
Fig. 10C

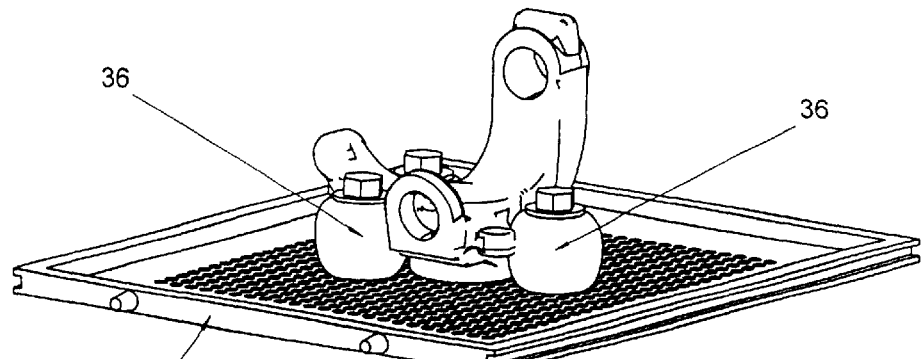
Fig. 11A
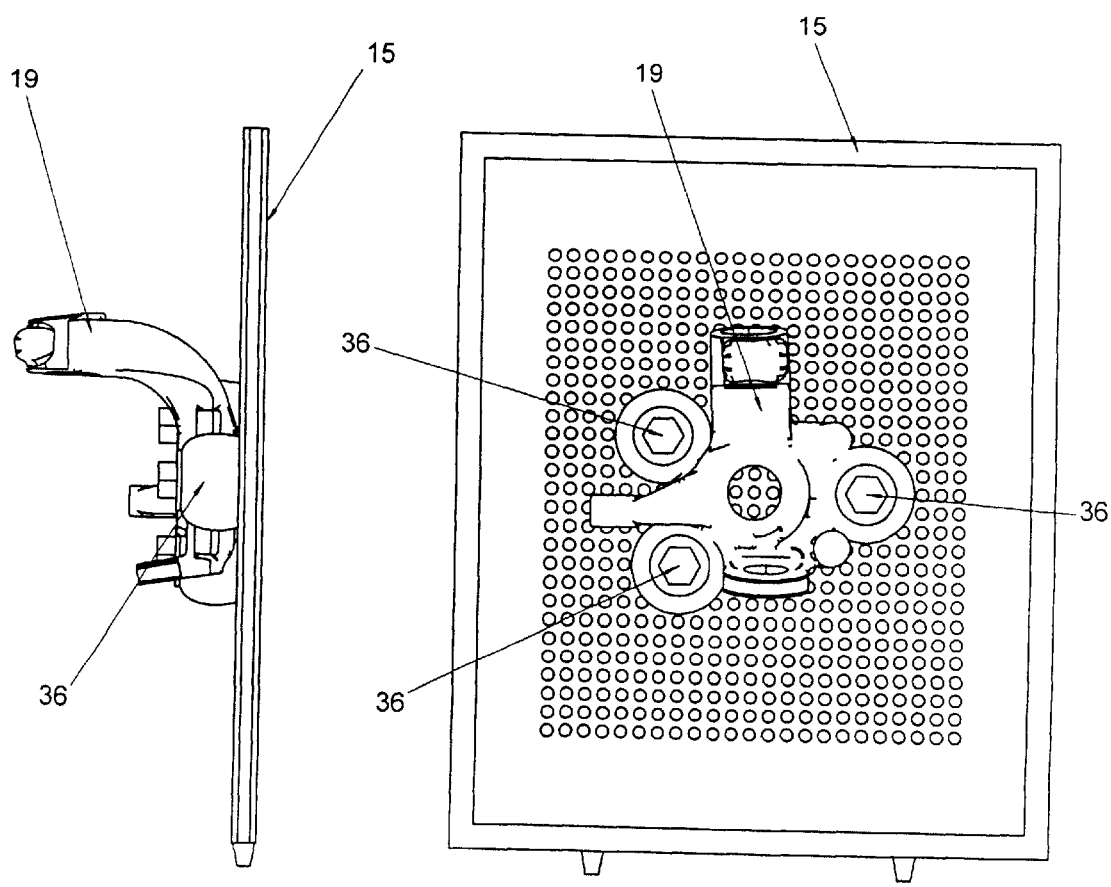
Fig. 11B
Fig. 11C

METHOD FOR INSPECTING OBJECTS PARTICULARLY FOR DETECTING DEFECTS OR IRREGULARITIES THEREIN BY MEANS OF X-RADIATION AND APPARATUS FOR PERFORMING THE METHOD

BACKGROUND OF THE INVENTION

1. Field of the Invention

The present invention relates to a method for inspecting or testing objects, particularly for detecting defects or irregularities therein, wherein the object to be inspected is moved in a rotary manner in an X-ray using a manipulating system, and the X-ray components, comprising X-ray tubes and X-ray detectors, are moved in a translatory manner, as well as to an apparatus for performing the method according to the invention.

2. Description of the Related Art

EP 984 301 A1 teaches a method for the inspection of luggage. The introduction to the aforementioned specification refers to fundamentally different possibilities for completely scanning an item of luggage.

Modern testing and inspecting systems for the detection of defects in castings and the like using X-rays operate according to two different principles, and the inspection object is either moved in the X-ray or the X-ray chain, comprising tube and detector, is moved around the object. In the first solution, the X-ray components are installed in a fixed manner, with the inspection object normally being grasped by a robot and moved into the x-ray beam. This makes it possible to inspect all positions of a part. In the second solution, the inspection object is stationary on a conveyor system, e.g. a pallet, and the X-ray components fixed to a C-arm or O-arc are moved around the inspection object.

In the first solution, the gripper gives rise to problems because in at least one position it is in the image and also the positioning precision is limited by wear and part tolerances. In addition, the costs of the robots are high compared with the overall installation.

In the second solution a very strong and therefore heavy, voluminous mechanism is required in order to bring the X-ray components into position in the short time available. In addition, the strong accelerations give rise to vibrations, which introduce blurring in the image and limit the inspection precision.

Therefore the problem of the invention is to improve the aforementioned method in such a way that it not only detects or recognizes smaller defects, but at the same time brings about a shorter inspection time with a very small physical size. The latter means that the mechanism must operate faster and with higher precision.

According to the invention, this problem is surprisingly solved in that the X-ray components are only moved in translatory manner and the test object or part is only moved in rotary manner in a cardan or gimbal suspension. In other words, the movement is divided up into a rotary inspection object movement and a translatory X-ray component movement. As a result, the necessary movements are minimized and, in particular, the rotation of larger masses far away from the center of gravity is prevented by the use of gimbal suspensions. The invention ensures that an inspection object can be moved in a translatory manner in the x-ray beam in one plane over the entire inspection object dimensions and in a rotary manner in all three axes with at least ±45°.

When using the X-ray detector, it is possible to use both an areal detector, such as an image intensifier or a flat panel detector (amorphous silicon detector), as well as a line detector. According to the invention, when using the line detector the drive in the X or Z-axis can be used for advancing the line detector for areal image generation.

The space requirement for an X-ray inspection device is a further important criterion. The characterized apparatus for performing the method only requires a limited amount of space and compared with conventional installations the space requirement is reduced by approximately 50%.

SUMMARY OF THE INVENTION

The invention provides a method for inspecting objects, for detecting defects or irregularities therein, using X-radiation, in which the object to be inspected is brought into different spatial positions and stays there during image detection, wherein the X-ray components, comprising an X-ray tube and an X-ray detector, are moved only in a translatory manner and the object is moved in a gimbal suspension in a rotary manner in at least one axis and at a maximum in three axes x, y and z.

The invention also provides an apparatus for performing an inspection of objects, comprising an X-ray tube positioned over an inspection object, which tube is fixed by means of a suspension to a rail and is capable of moving in a translatory manner; an X-ray detector under the inspection object which detector is fixed to a rail and is capable of moving in a translatory manner; wherein the inspection object is placed and fixed on one or more pallets, which are connected with gimbal frames for the rotation of the inspection object in all three axes x, y and z.

The invention further provides a method for inspecting an object, which comprises the steps of:

a) providing a device for inspecting an object, which device comprises:
  i) a radiation protection cabin having an inside and an outside,
  ii) at least one translatory movement unit attached to the inside of the radiation protection cabin, which translatory movement unit comprises one or more rails;
  iii) one or more object support pallets within the radiation protection cabin, which support pallet or pallets are connected with gimbal frames, and which gimbal frames are attached to drives and are capable of moving or tilting the pallet or pallets;
  iv) an X-ray tube fixed to a rail of the translatory movement unit, which X-ray tube is suspended above the pallet or pallets, and which X-ray tube is capable of moving in a translatory manner along the rail;
  v) an X-ray detector fixed to a rail of the translatory movement unit, which X-ray detector is present under the pallet or pallets, and which X-ray detector is capable of moving in a translatory manner along the rail;

b) providing at least one test object, and placing the test object on the pallet or pallets such that the object is beneath the X-ray tube and above the X-ray detector; and c) subjecting the test object to X-radiation in a plurality of spatial positions to thereby detect an image of the test object in each spatial position, wherein the X-ray tube and the X-ray detector are moved only in a translatory manner, and wherein the test object is moved in a gimbal suspension in a rotary manner in at least one axis and in a maximum of three axes x, y, and z.

The invention still further provides a device for inspecting an object, which device comprises:

i) a radiation protection cabin having an inside and an outside, ii) at least one translatory movement unit attached to the inside of the radiation protection cabin, which translatory movement unit comprises one or more rails;

iii) one or more object support pallets within the radiation protection cabin, which support pallet or pallets are connected with gimbal frames, and which gimbal frames are attached to drives and are capable of moving or tilting the pallet or pallets;

iv) an X-ray tube fixed to a rail of the translatory movement unit, which X-ray tube is suspended above the pallet or pallets, and which X-ray tube is capable of moving in a translatory manner along the rail; and v) an X-ray detector fixed to a rail of the translatory movement unit, which X-ray detector is present under the pallet or pallets, and which X-ray detector is capable of moving in a translatory manner along the rail.

BRIEF DESCRIPTION OF THE DRAWINGS

FIGS. 9A–9C show different diagrammatic views concerning the arrangement of the inspection object on the pallet.

FIGS. 10A–10C show different diagrammatic views concerning the clamping fastening of the inspection object to the pallet.

FIGS. 11A–11C show different diagrammatic views, like FIGS. 9 and 10, which show a raster for fastening and moving the inspection object on the pallet.

DETAILED DESCRIPTION OF THE PREFERRED EMBODIMENT

Figure 1:
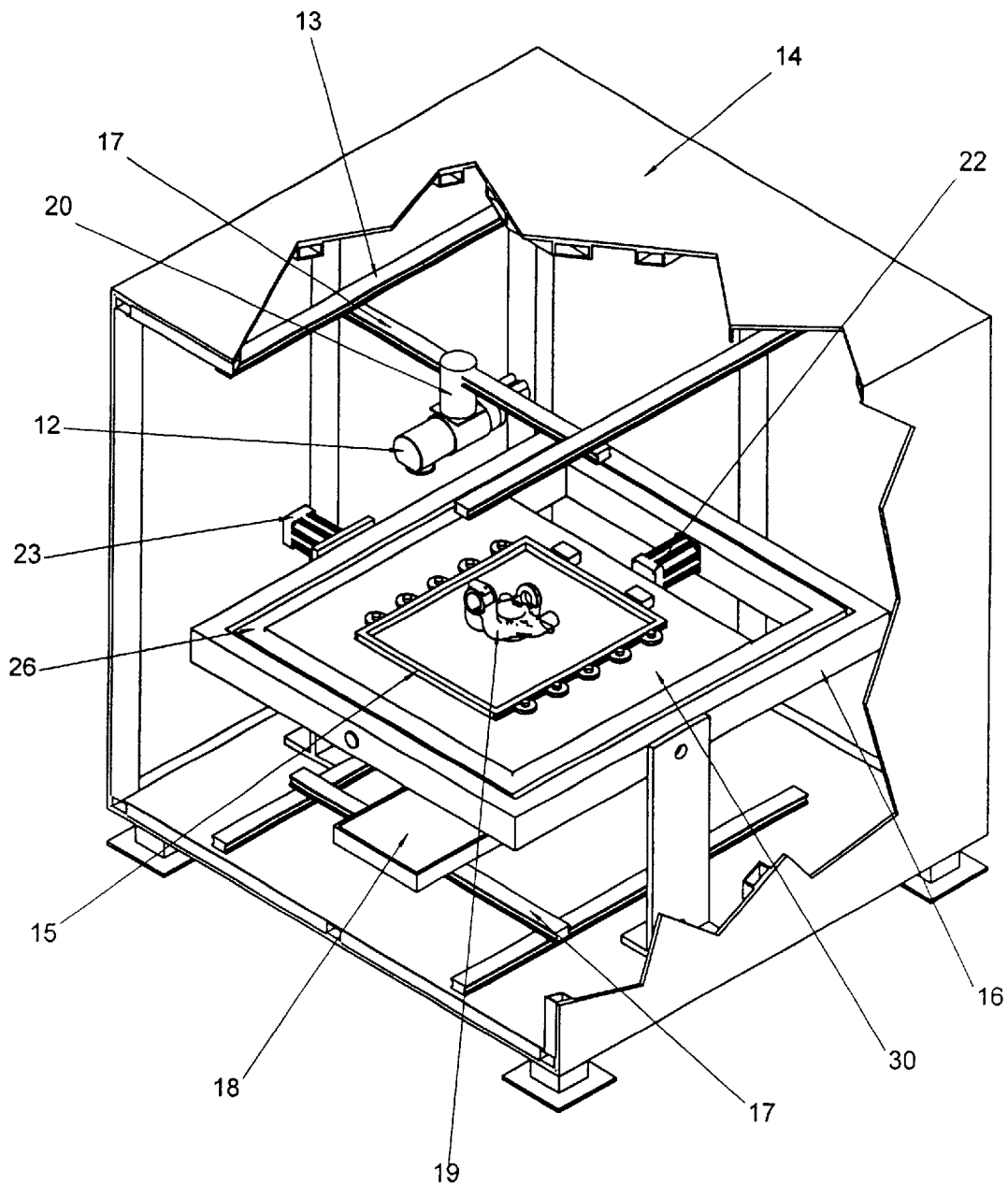
FIG. 1 shows a perspective view of the apparatus according to the invention, in which parts are broken away in order to show the internal structure.

FIG. 1 shows the fundamental structure of an apparatus according to the invention enabling the method of the invention to be performed. The test or inspection system comprises a radiation protection cabin 14, an X-ray tube 12, an X-ray detector 18, a part support/pallet 30, and an inspection/test object 19. Although FIG. 1 shows only one inspection object on a pallet 15, there can also be several objects on a single pallet. FIG. 1 also shows gimbal frames 16 and 26, and drives 22 and 23 for the gimbal or cardan axes in the vicinity of the center of gravity, x-y plane translatory movement units 17 and 13 for the tube and detector in the X and Z-direction, both on the base and below the cover.

The testing or inspection sequence is as follows:

The parts or objects are conveyed into the cabin and the radiation protection, e.g. a radiation protection cabin door, is closed. The X-ray is switched on and there is a move up to the first inspection position for the first inspection object. For this purpose, the tube and detector are brought into the appropriate position. The drives of these translatory axes can be coupled, so that the beam always strikes perpendicularly in the center of the detector. Simultaneously, using the two drives 22 and 23, the frame is tilted in such a way that the correct transmission angle for the inspection object is reached. Since, as will be shown hereinafter, the objects are fixed to the pallet, angles above 45° are possible without the object sliding. The two frames are balanced in such a way that virtually no forces are required in order to maintain the positions reached. The detector is used for taking an image and it is passed onto a screen or computer for evaluation purposes. Then, in parallel, the tube and the detector are moved to the next position and the two frames are tilted in the correct angle. The next image is then taken. This procedure is repeated until the object or all the objects on the pallet have been inspected. This method makes it possible to achieve the necessary transmission angles and to move to all positions.

In order to be able to adjust the magnification, i.e. the distance between tube and inspection object and inspection object and detector, optionally there can be a manual or automatic adjustment 20 of the tube in the vertical direction.

Figure 2:
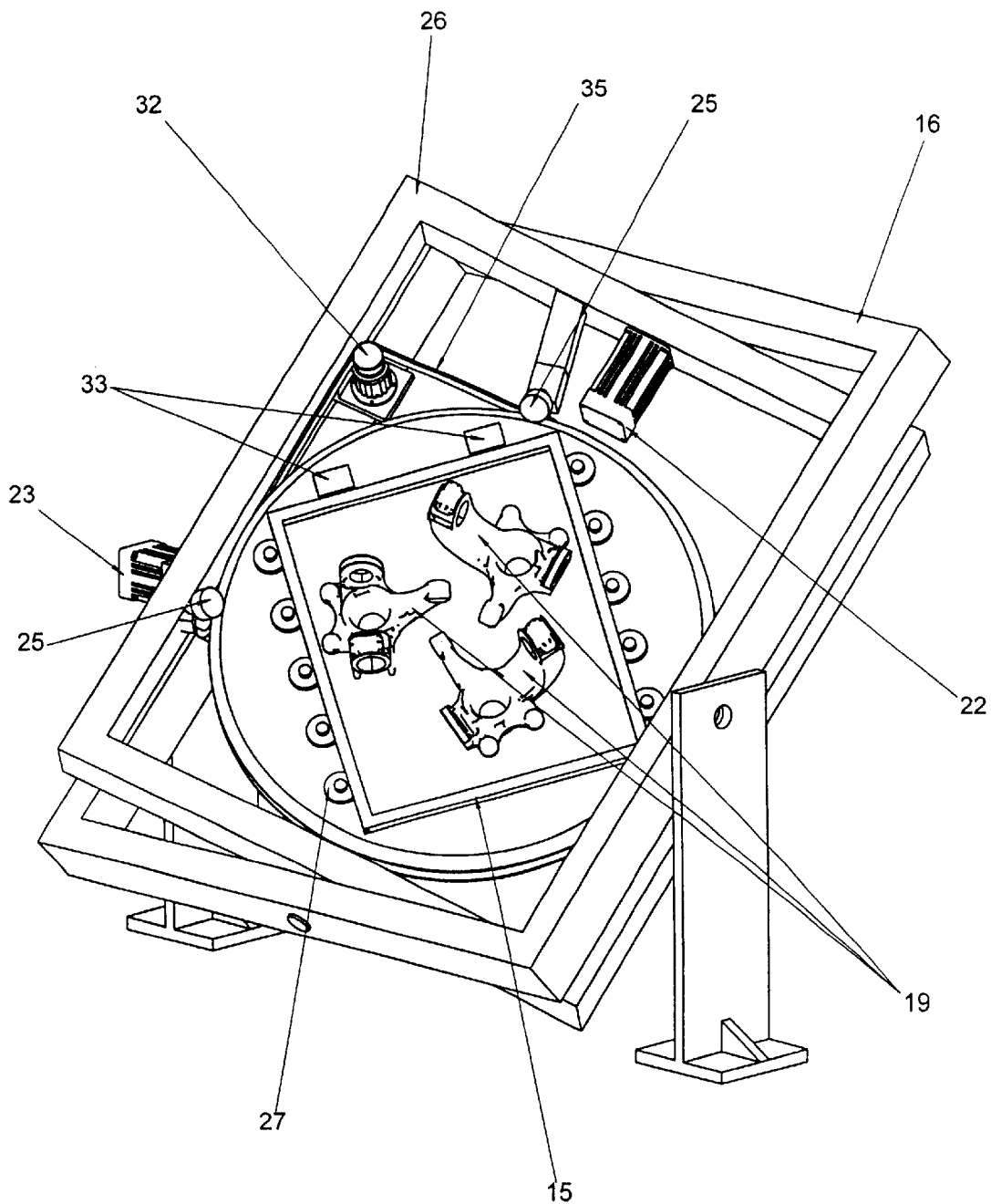
FIG. 2 shows a perspective view of the gimbal or cardan frame with fixed inspection objects.
Figure 3A:
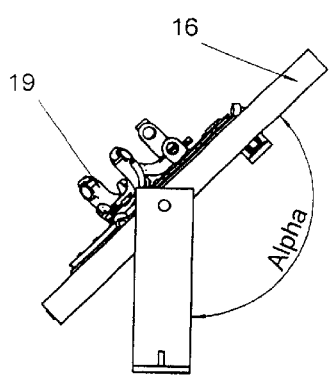
FIGS. 3A–3B show different diagrammatic views making clear the gimbal suspension.
Figure 3D:
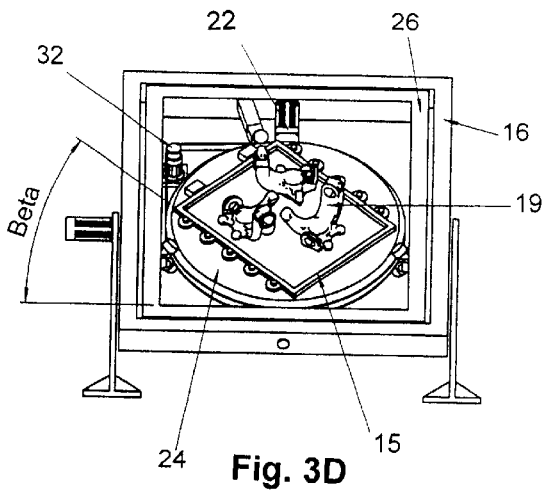
Figure 3B:
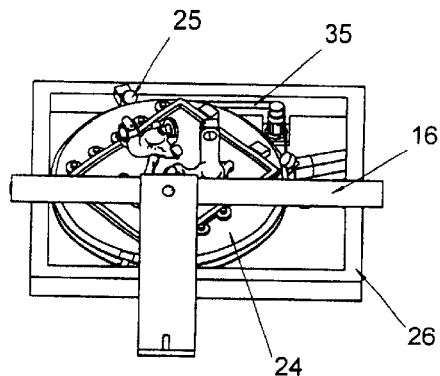
Figure 3E:
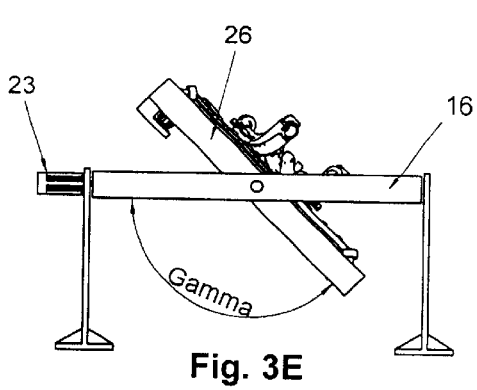
Figure 3C:
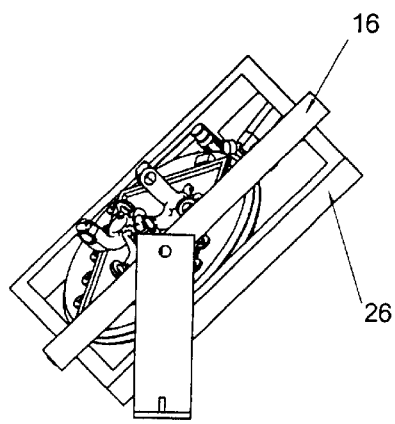
Figure 3F:
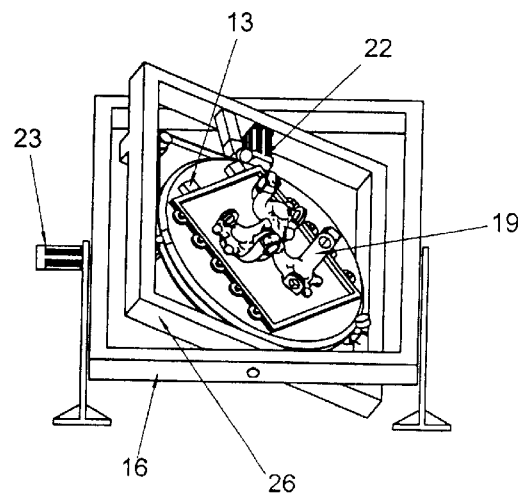

The inspection time can be significantly reduced by placing several inspection objects on one pallet, because the conveying in and out time is divided up over several objects. If a rotary turntable is used for receiving the pallet, several identical inspection objects can be inspected with the same transmission images on a single pallet and simultaneously it is possible to additionally dynamically vary the distance between the inspection object and the tube and detector. FIG. 2 shows an embodiment with three identical inspection objects 19. It is important that there is no central guidance of the turntable, because such a central guidance and optionally the drives would be located in the X-ray and would inadmissibly restrict the transmission angle for the inspection objects. In FIG. 2, the turntable is fixed to at least three pairs of rollers 25, in this case displaced by approximately 120° and is driven by the motor 32 by means of a belt 35. The pallet 15 with the inspection objects 19 on it is fixed, for example, by lateral guide rollers 27 and two electromagnets 33.

FIG. 3 shows the tilting in each case in one direction about the two axes and the rotation possibilities from in each case two sides.

Figure 4:
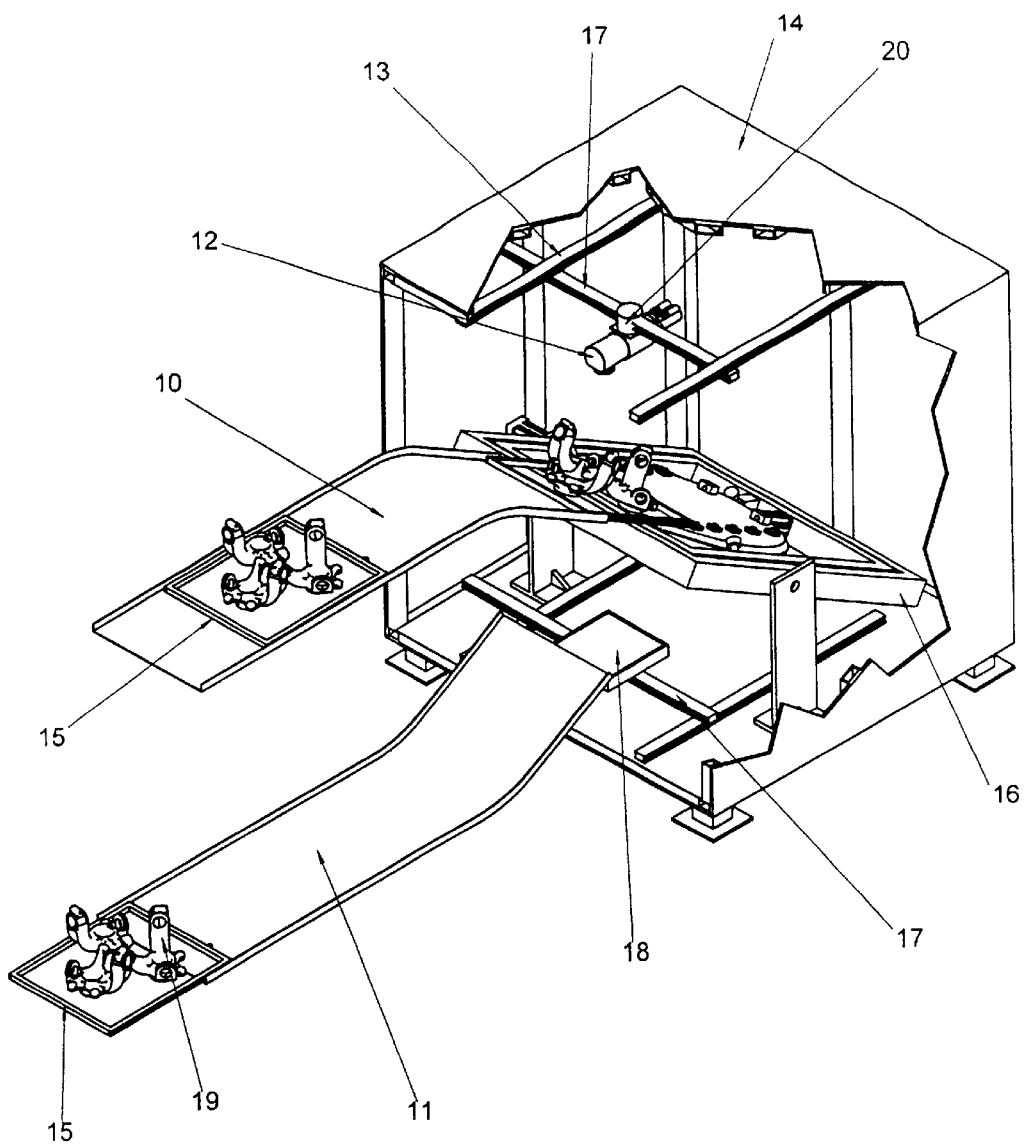
FIGS. 4 and 5 show perspective views of the apparatus according to the invention shown in FIG. 1, in which parts are broken away in order to show the feed conveying system, with different positions of the gimbal frame.

Conveying in and out takes place in the following manner:

For inspection purposes the inspection objects are placed on pallets 15. As shown in FIG. 4, the pallets can be actively driven on a conveying system 10, 11 or can be conveyed in and out using gravity. Several pallets can be provided in the system, so that the loading, the conveying in front of the cabin, the actual inspection in the cabin, and the unloading can take place simultaneously.

For conveying a pallet into the cabin, the gimbal frame 16 and turntable 24 are brought into the position shown in FIG.

4. The pallet, which has waited directly in front of the cabin, is either driven or moved by gravity on the turntable into the cabin. The precise end position is ensured by two or more centering pins and at least one (here two) electromagnets. On the pallet, permanent magnets can face the electromagnets so that a force can be applied for conveying out by reversing the polarity of the electromagnets.

Figure 5:
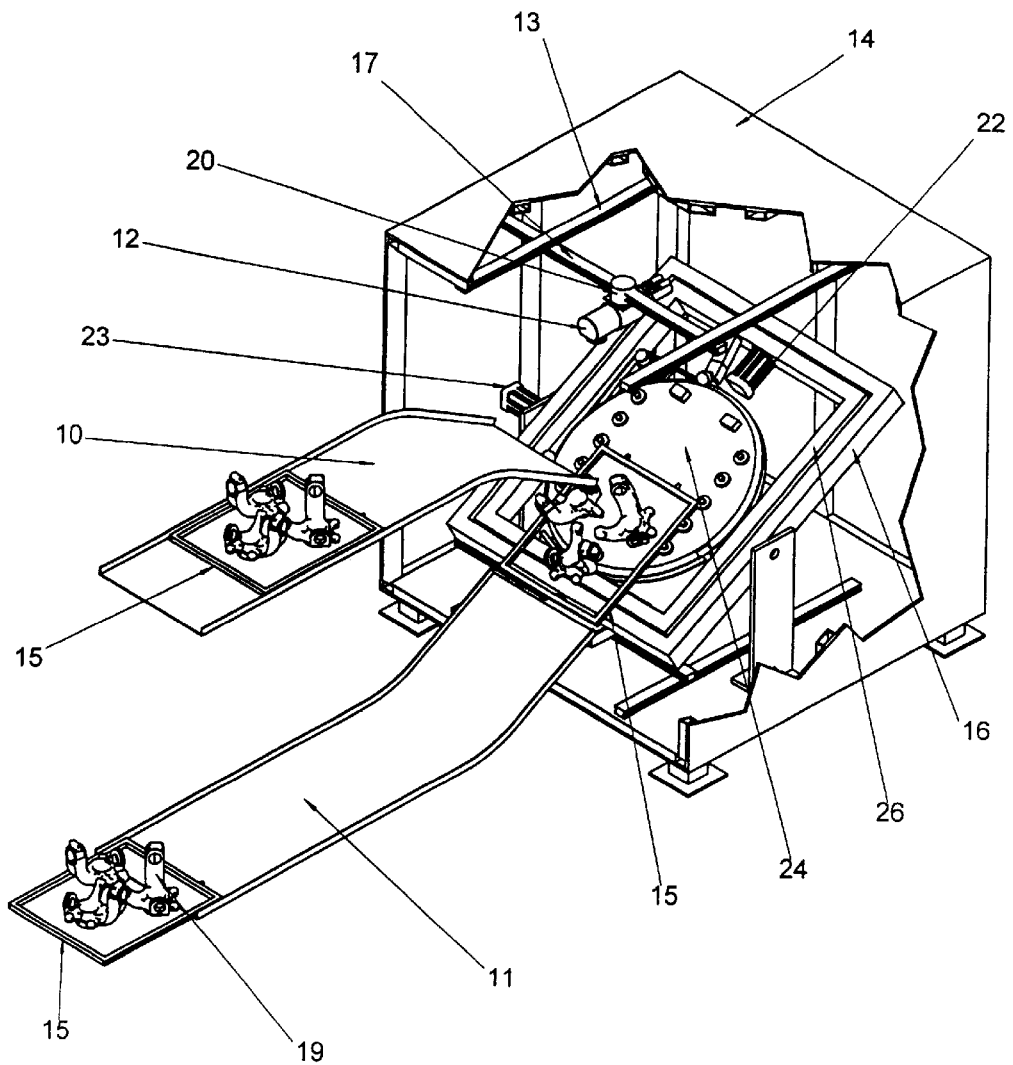

For conveying out or discharging, the frame and turntable are brought into the position shown in FIG. 5. The pallet on the turntable is brought onto the lower conveying system 11 by polarity reversal of the electromagnet (release of fixing and acceleration) and by utilizing gravity and then by means of the conveying system 11 is conveyed away for pallet discharge purposes.

Figure 6:
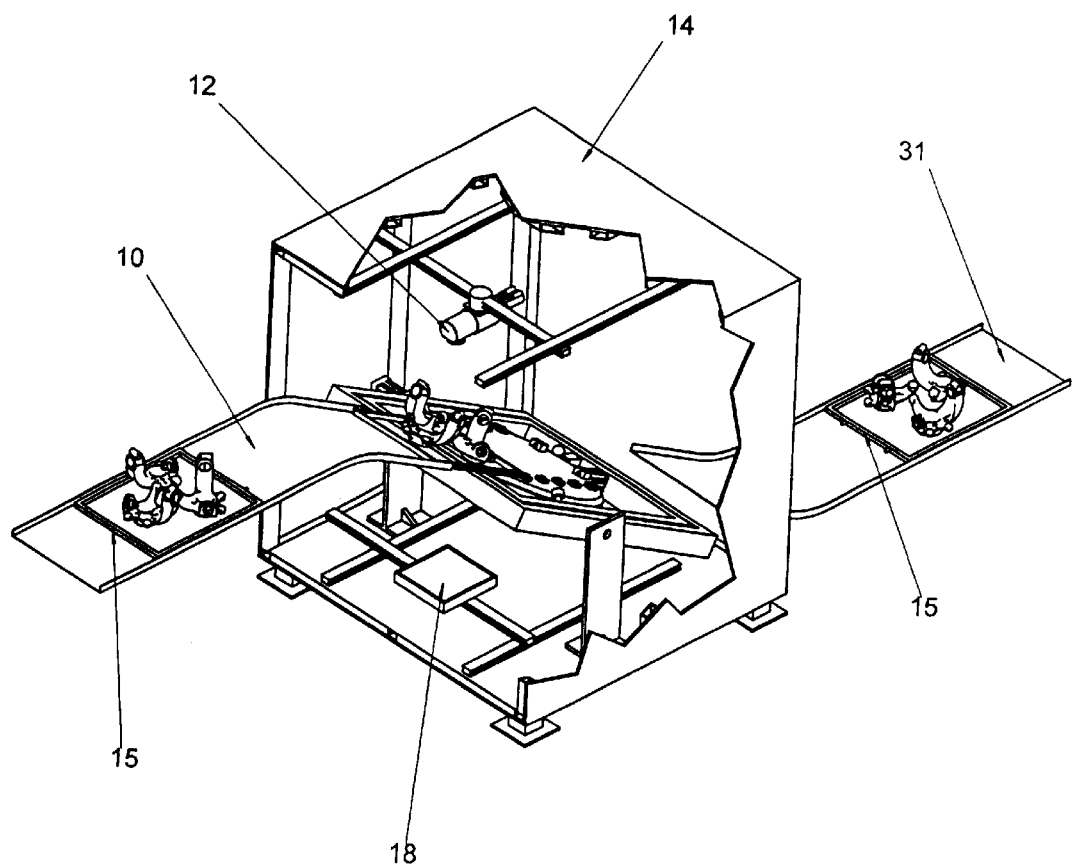
FIG. 6 shows a perspective view of the apparatus according to the invention shown in FIG. 1, in which parts are shown broken away in order to better illustrate the supply and discharge conveyors.

In other applications, it is not possible that the conveying in and out is on the same side, and a through-conveying system is necessary. FIG. 6 shows how the method can be implemented on the basis of the preceding installation. The conveying out unit 31 is now fitted to the side opposite to the conveying in unit 10. For conveying out the pallet is rotated in such a way that a rearwardly downward extraction is possible. When the pallet has left the turntable, the latter is rotated by 180° and is ready for receiving the next pallet from the front.

Figure 7:
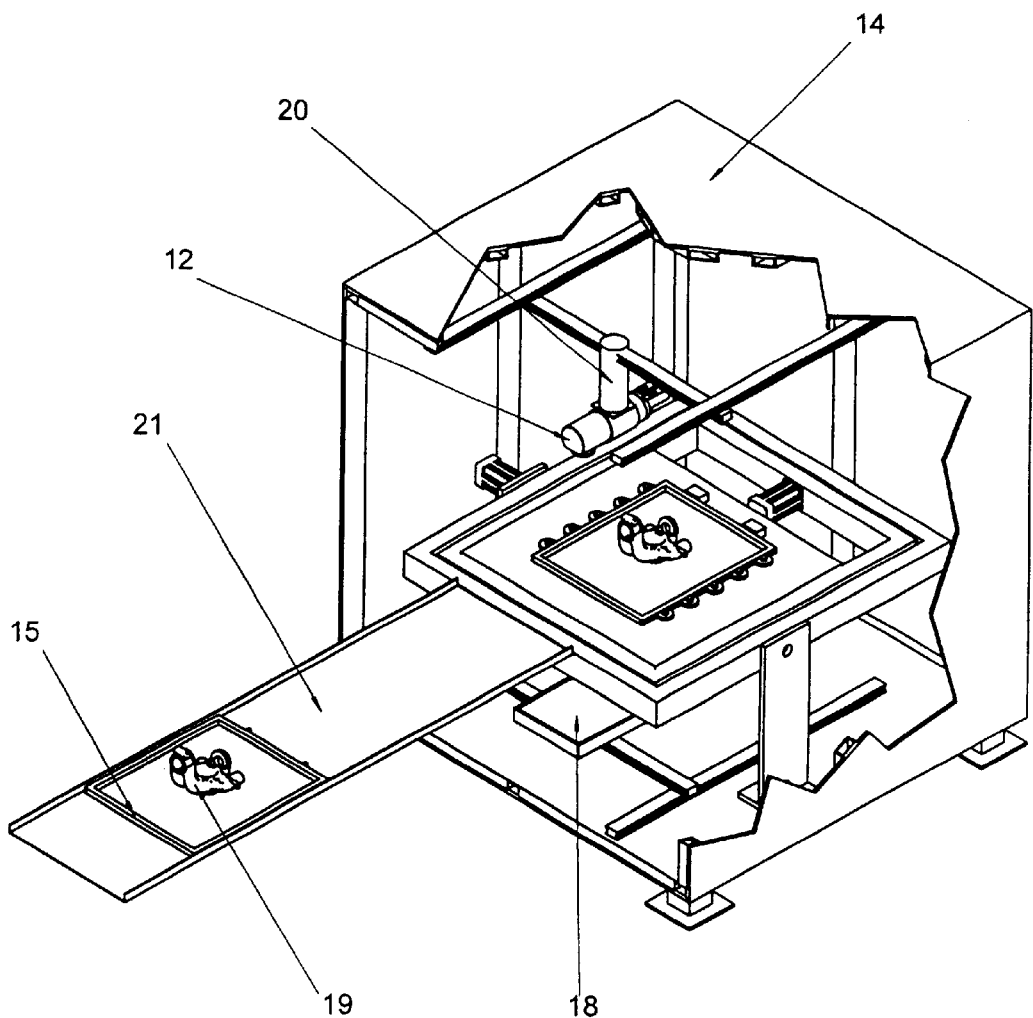
FIG. 7 shows a perspective view of the apparatus according to the invention, in which parts are shown broken away in order to illustrate the supply conveyor.

If gravity is not to be used for conveying in and out purposes or a purely horizontal conveying is required, e.g. due to the pallet loading height, solutions are conceivable in which conveying in and out take place horizontally. The pallets 15 must be driven or have their own drive. FIG. 7 shows an example with a horizontal conveying in unit 21

The objects are fixed to the pallets in the following manner:

In order to permit tilting of the frame with no effect on the position of the objects, it is necessary for the objects to be reliably fixed to the pallets. There are two different fixing possibilities.

Figure 8A:
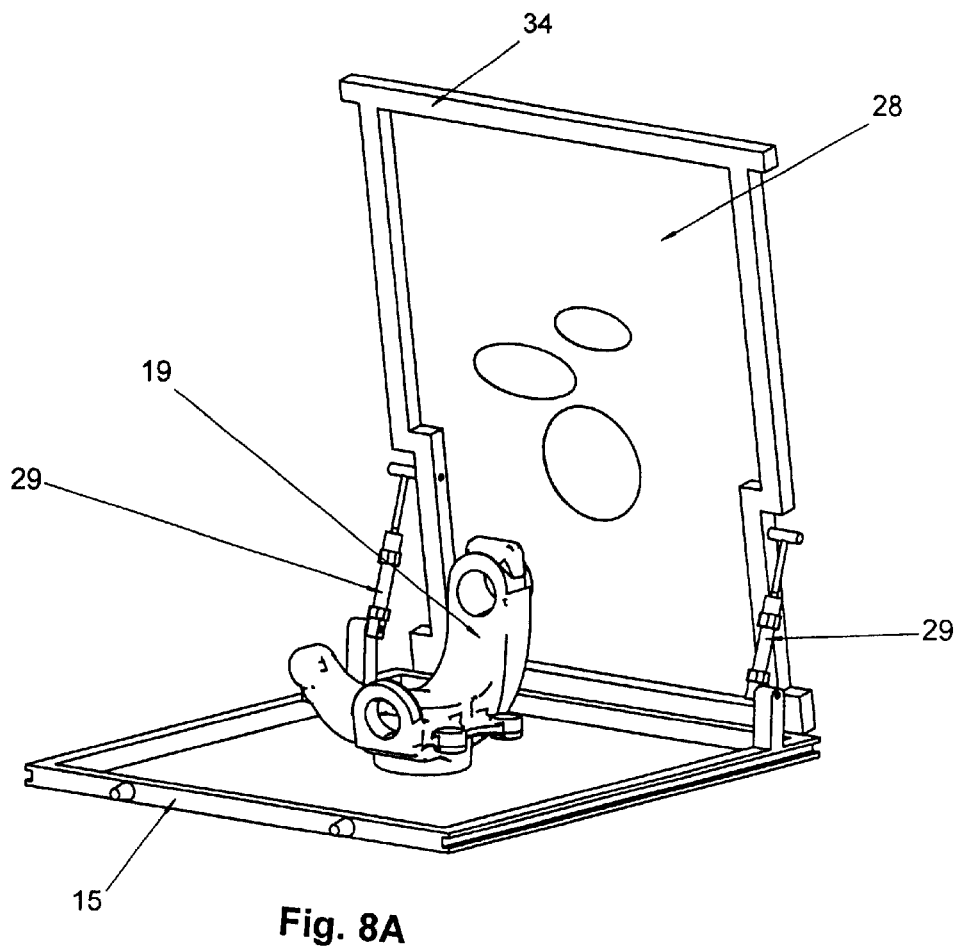
FIGS. 8A–8B show perspective views of an inspection object placed or fixed on the pallet.
Figure 8B:
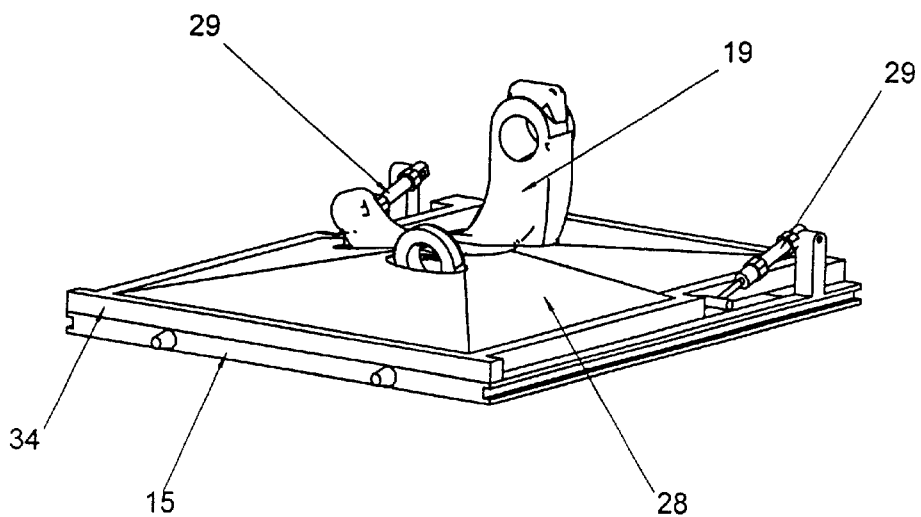

As shown in FIG. 8, in the case of the first possibility a frame is drawn with an elastic, but stable membrane 28 over the pallet and holds the object 19 in its correct position. After placing the test objects on the pallet, on conveying in the cover 34 is automatically closed and locked with a lock (car tailgate principle). Optionally, the fulcrum point of the spring-damper system can be higher on closing. Then by a spring-damper system 29, a force is applied for forcing down the frame, making a separate locking system unnecessary. On conveying into the cabin during inspection and on conveying out, the cover remains closed. After conveying out, the locking system is released or, in the case of a high fulcrum point for the cover, is raised above the pressure point and the cover opens automatically due to the spring tension of the gas pressure damper 29 enabling the objects to be removed.

According to FIG. 9, the second possibility provides for several elastic fixing buffers 36, which can optionally have different sizes and shapes, which are applied at appropriate points to the contour of the inspection objects 19 on pallet 15. They are constructed in such a way that by the application of a force the horizontal extension can increase and as a result the object is clamped, as shown in FIG. 10. Due to the locking system known from ball pens, clamping is maintained until once again a force is applied and the clamping action cancelled. The object can now be removed. Through a suitable number and positioning of the fixing buffers, in principle any inspection object can be appropriately fixed. It plays no part whether there is only one or several objects fixed to a pallet.

For simplification purposes in the case of the second solution, it is also possible to provide pallets with a fixed raster and use the fixing buffers there or to rapidly move the same in the case of other inspection objects. This is shown in FIG. 11.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A method for inspecting objects, for detecting defects or irregularities therein, using X-radiation, in which the object to be inspected is brought into different spatial positions and stays there during image detection, wherein the X-ray components, comprising an X-ray tube and an X-ray detector, are moved only in a translatory manner and the object is moved in a gimbal suspension in a rotary manner in all three axes x, y and z.

2. The method according to claim 1, wherein the translatory movement of the X-ray tube is coupled with that of the X-ray detector.

3. The method according to claim 2, wherein coupling takes place mechanically or in a program-controlled manner.

4. The method according to claim 1, wherein the X-ray tube can be vertically adjusted either manually or by a motor for setting the magnification.

5. The method according to claim 1, wherein pallets receiving the inspection objects are conveyed in and/or out using the force of gravity on the same or opposite side of a radiation protection cabin.

6. An apparatus for performing an inspection of objects, comprising an X-ray tube positioned over an inspection object, which tube is fixed by means of a suspension to a rail and is capable of moving in a translatory manner; an X-ray detector under the inspection object which detector is fixed to a rail and is capable of moving in a translatory manner; wherein the inspection object is placed and fixed on one or more pallets, which are connected with gimbal frames for the rotation of the inspection object in all three axes x, y and z.

7. The apparatus according to claim 6, wherein the pallet is fixed on a turntable by means of guide rollers and electromagnets.

8. The apparatus according to claim 6, wherein the pallets are fixable with respect to the turntable by means of permanent magnets.

9. The apparatus according to claim 6, wherein the inspection objects are fixed to the pallet by means of elastic flap covers with closure means and/or pneumatic springs and/or lockable elastic fixing buffers.

10. The apparatus according to claim 6, wherein the pallets have a raster for receiving fixing buffers.

11. A method for inspecting an object, which comprises the steps of:
 a) providing a device for inspecting an object, which device comprises:
  i) a radiation protection cabin having an inside and an outside,
  ii) at least one translatory movement unit attached to the inside of the radiation protection cabin, which translatory movement unit comprises one or more rails;
  iii) one or more object support pallets within the radiation protection cabin, which support pallet or pallets are connected with gimbal frames, and which gimbal frames are attached to drives and are capable of tilting the pallet or pallets;

iv) an X-ray tube fixed to a rail of the translatory movement unit, which X-ray tube is suspended above the pallet or pallets, and which X-ray tube is capable of moving in a translatory manner along the rail;

v) an X-ray detector fixed to a rail of the translatory movement unit, which X-ray detector is present under the pallet or pallets, and which X-ray detector is capable of moving in a translatory manner along the rail;

b) providing at least one test object, and placing the test object on the pallet or pallets such that the object is beneath the X-ray tube and above the X-ray detector; and c) subjecting the test object to X-radiation in a plurality of spatial positions to thereby detect an image of the test object in each spatial position, wherein the X-ray tube and the X-ray detector are moved only in a translatory manner, and wherein the test object is moved in a gimbal suspension in a rotary manner in all three axes x, y, and z.

12. The method of claim 11 further comprising the step of evaluating the image of the test object with a computer.

13. The method of claim 11 wherein the object is fixed to the pallet.

14. The method according to claim 11, wherein the translatory movement of the X-ray tube is coupled with the translatory movement of the X-ray detector.

15. The method according to claim 14, wherein coupling takes place mechanically or in program-controlled manner.

16. A device for inspecting an object, which device comprises:

i) a radiation protection cabin having an inside and an outside, ii) at least one translatory movement unit attached to the inside of the radiation protection cabin, which translatory movement unit comprises one or more rails;

iii) one or more object support pallets within the radiation protection cabin, which support pallet or pallets are connected with gimbal frames, and which gimbal frames are attached to drives and are capable of tilting the pallet or pallets in all three axes x, y, and z;

iv) an X-ray tube fixed to a rail of the translatory movement unit, which X-ray tube is suspended above the pallet or pallets, and which X-ray tube is capable of moving in a translatory manner along the rail; and v) an X-ray detector fixed to a rail of the translatory movement unit, which X-ray detector is present under the pallet or pallets, and which X-ray detector is capable of moving in a translatory manner along the rail.

17. The device of claim 16 further comprising an upper conveying system.

18. The device of claim 16 further comprising a lower conveying system.

19. The device of claim 16 wherein said pallet is fixed on a turntable.

20. The device of claim 19 wherein said turntable has no central guidance means.

* * * * *